(12) United States Patent
Pinchassi Dar et al.

(10) Patent No.: US 7,331,449 B2
(45) Date of Patent: Feb. 19, 2008

(54) COMBINED CONTACT LENS CASE AND SOLUTION STORAGE DEVICE

(76) Inventors: Eli Pinchassi Dar, 35-02 Hillside Ter., Fair Lawn, NJ (US) 07410; Irit Dar, 35-02 Hillside Ter., Fair Lawn, NJ (US) 07410

( * ) Notice: Subject to any disclaimer, the term of this patent is extended or adjusted under 35 U.S.C. 154(b) by 704 days.

(21) Appl. No.: 10/783,298

(22) Filed: Feb. 20, 2004

(65) Prior Publication Data

US 2005/0186128 A1    Aug. 25, 2005

(51) Int. Cl.
*A45C 11/04*    (2006.01)
(52) U.S. Cl. .......................................... 206/5.1; 134/901
(58) Field of Classification Search .................. 206/5.1, 206/223, 570, 581, 5, 6; 134/901; 294/1.2; 222/207; 422/300
See application file for complete search history.

(56) References Cited

U.S. PATENT DOCUMENTS 4,574,944 A * 3/1986 Gregory ..................... 206/5.1
4,905,819 A * 3/1990 Clements et al. ............ 206/5.1
5,375,699 A * 12/1994 Amend ....................... 206/5.1
5,381,889 A * 1/1995 Amend ....................... 206/5.1
6,289,906 B1 * 9/2001 Vanden Dries et al. ..... 134/117
2004/0173474 A1 * 9/2004 Haggin ....................... 206/5.1
2004/0251146 A1 * 12/2004 Church et al. ............... 206/5.1

* cited by examiner

*Primary Examiner*—Mickey Yu
*Assistant Examiner*—Steven A. Reynolds
(74) *Attorney, Agent, or Firm*—Wolf Block Schorr & Solis-Cohen LLP

(57) ABSTRACT

Storage device for storing contact lenses and contact lens solution including a case defining a reservoir for contact lens solution and a pair of contact lens retaining compartments for retaining contact lenses. The case includes a mechanism for causing a stream of contact lens solution to flow from the reservoir to an exterior of the case (for use when rinsing and/or cleaning the contact lens) and another mechanism for causing the contact lens solution to flow from the reservoir into the compartments (for use when storing the contact lenses in the compartments). These mechanisms can be alternatively enabled depending on the particular use sought for the contact lens solution.

26 Claims, 14 Drawing Sheets

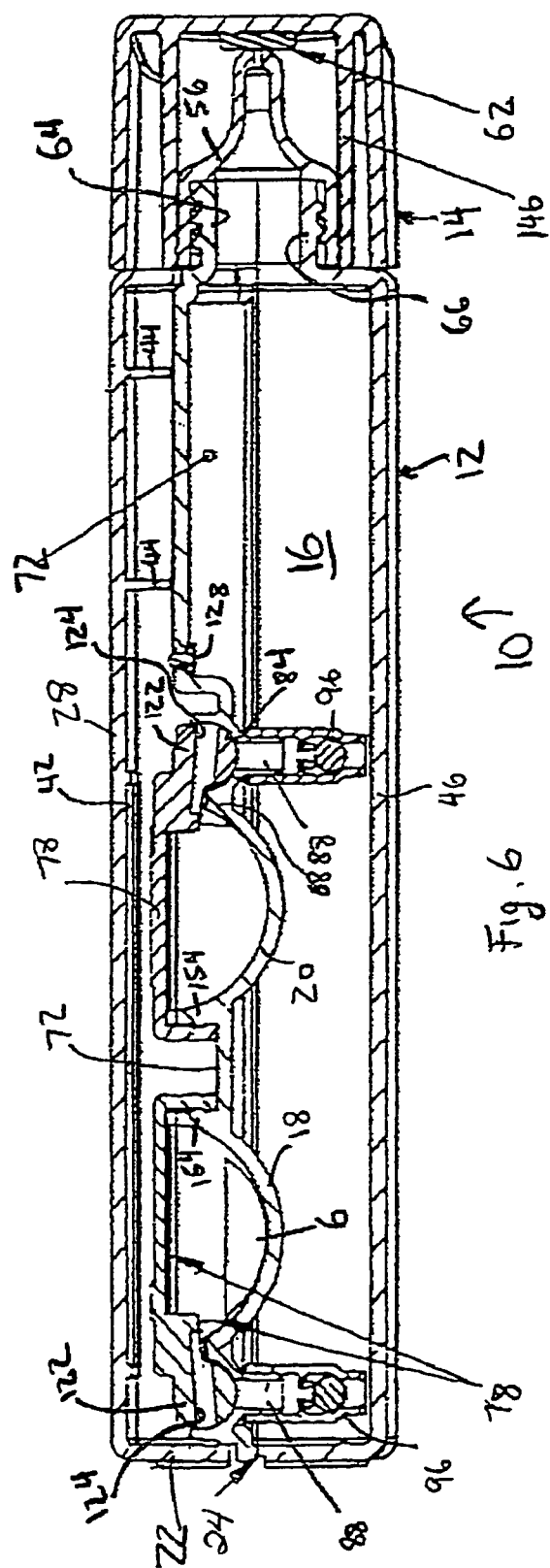
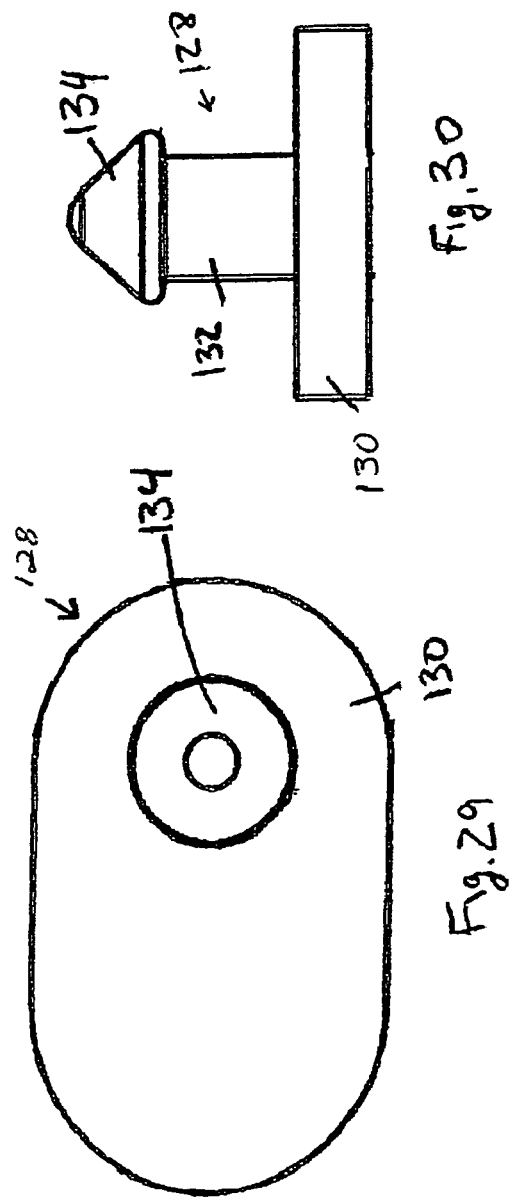
Fig. 6
Fig. 29
Fig. 30

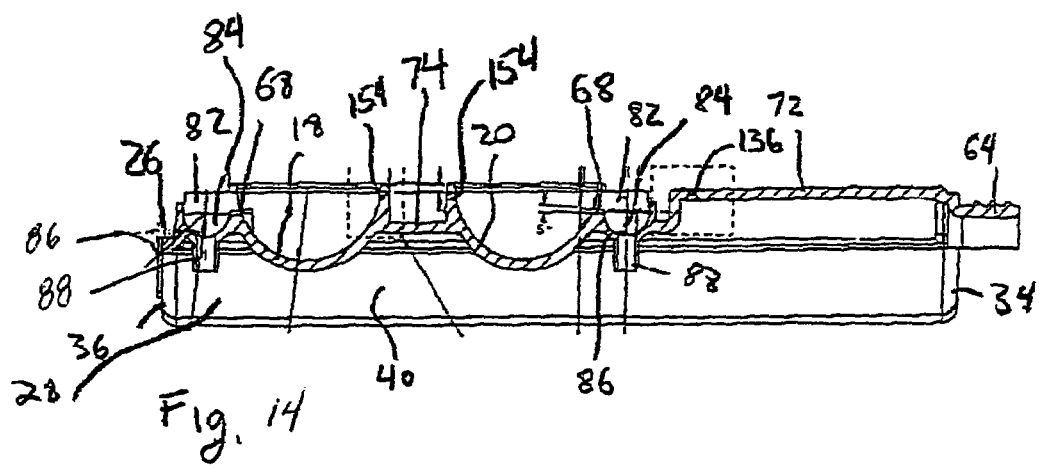
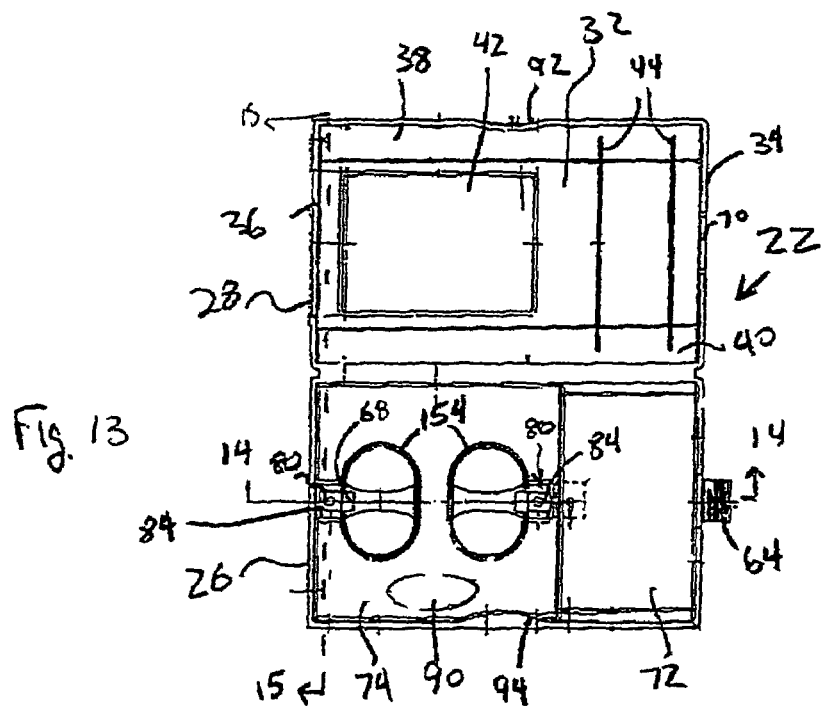
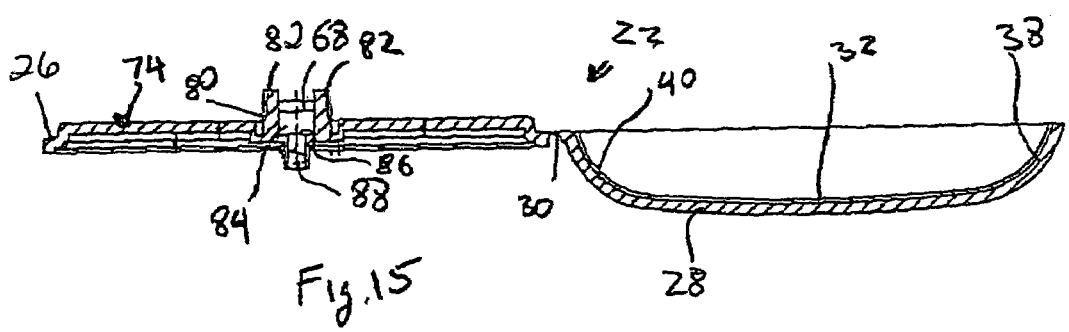

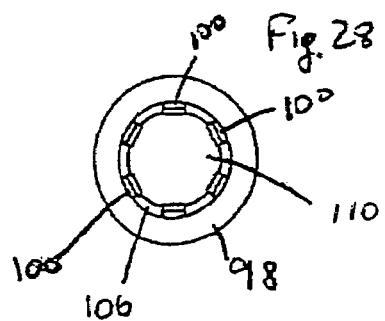
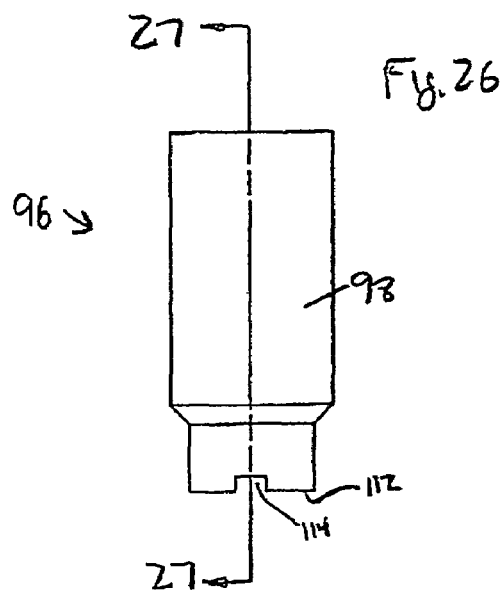
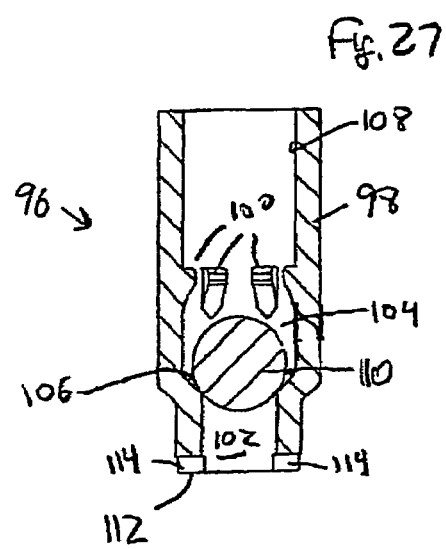
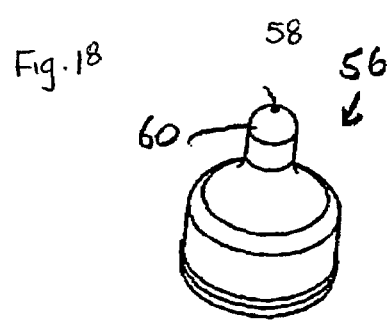
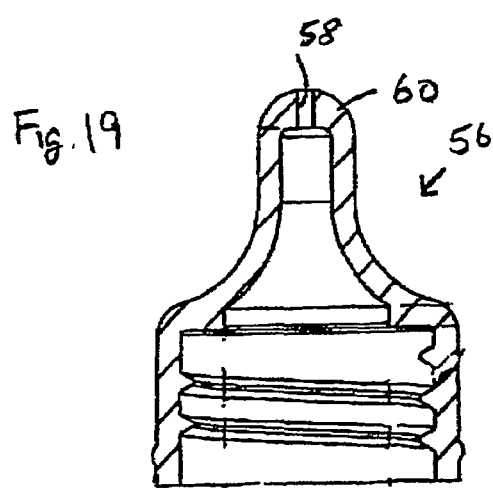

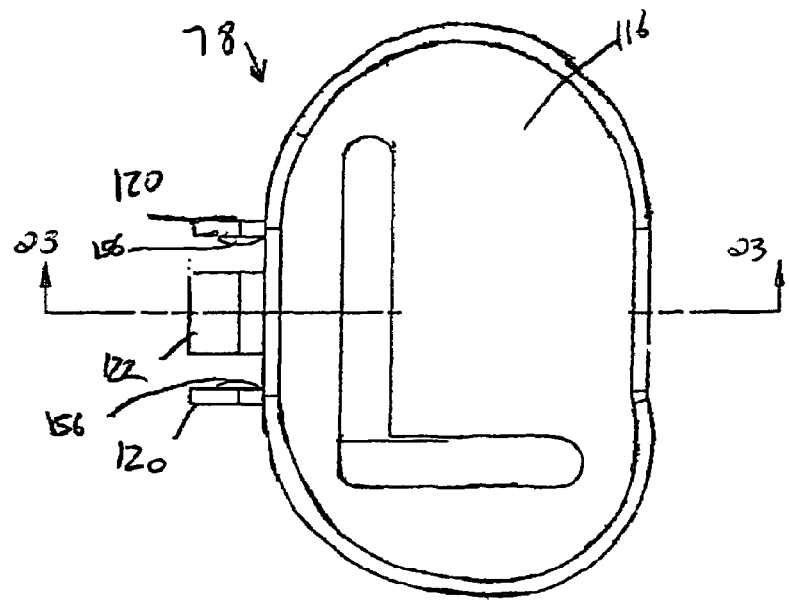
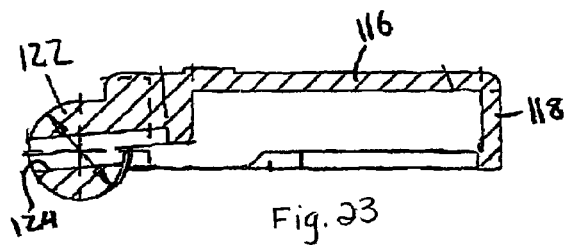
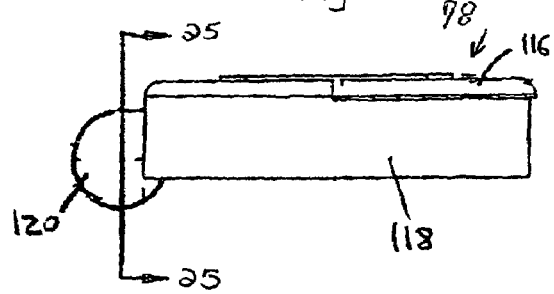
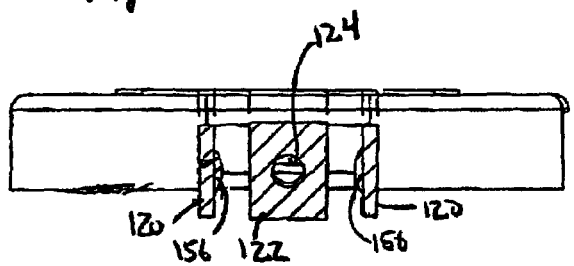

COMBINED CONTACT LENS CASE AND SOLUTION STORAGE DEVICE

FIELD OF THE INVENTION

The present invention relates generally to a storage device for contact lenses and more particularly to a contact lens storage device which includes a pair of compartments for receiving contact lenses and a separate storage compartment in which rinsing or cleaning solution can be stored for possible use in rinsing and/or cleaning the contact lenses when the contact lenses are placed into the compartments after use or removed from the compartments before use.

BACKGROUND OF THE INVENTION

There are various constructions of contact lens storage devices which include a separate storage compartment for storing a rinsing solution, cleaning solution or other solution to be applied to the contact lenses. All such solutions which can be applied to contact lenses to clean, rinse, sterilize, condition or otherwise treat the contact lenses will be referred to herein as a contact lens solution.

One such storage device is shown in U.S. Des. Pat. No. 390,356 (Fortier) and includes a cylindrical squeeze-bottle of contact lens solution with nozzles at both ends, a cylindrical contact lens case mounted on each end of the solution bottle via threads located on each end and a cap for covering each contact lens case. Each contact lens case appears to be fillable with contact lens solution from the squeeze-bottle by squeezing the solution bottle.

Another contact lens storage device is shown in U.S. Pat. No. 4,721,124 (Tuerkheimer et al.) and includes a container for housing a pair of lens carriers which hold a pair of contact lenses and a base/pump housing connected to the bottom of the container for retaining cleaning fluid. A pump mechanism propels the cleaning fluid into the cleaning chamber. In use, the base/pump housing is filled with contact lens solution and then the contact lenses are placed into the lens carriers. The bottom wall of the base/pump housing is pressed to force contact lens solution through apertures into the lens carriers.

U.S. Pat. No. 5,347,674 (Gabbert) describes another contact lens storage device including a pair of lens containers and a fluid reservoir for housing contact lens solution. The reservoir is in fluid communication with the lens containers such that the contact lens solution may travel through a channel into the lens containers. The fluid reservoir can be replenished with contact lens solution via a hole formed in the fluid reservoir.

U.S. Pat. No. Des. 331,588 (Ives) shows a combination vial, tray and case for contact lenses and contact lens solution.

U.S. Pat. No. 5,381,889 (Amend) describes a container for contact lenses and for a supply of contact lens fluid having a base body with a receptacle for a removable contact lens case, a fluid chamber for the contact lens fluid, and a metering connector fastened on the fluid chamber to purportedly fill the contact lens ease with fluid.

OBJECTS AND SUMMARY OF THE INVENTION

It is an object of the present invention to provide a new and improved storage device for contact lens.

It is another object of the present invention to provide a new and improved contact lens storage device which includes, in addition to a pair of compartments for receiving contact lenses, a separate storage compartment in which contact lens solution can be stored. This enables a single device to retain the contacts lenses and contact lens solution so that the contact lens solution is readily available for possible use in rinsing and/or cleaning the contact lenses when the contact lenses are placed into the compartments after use or are removed from the compartments before use.

It is still another object of the present invention to provide a new and improved contact lens storage device which includes a storage compartment for contact lens solution underneath contact lens retaining compartments and is constructed to provide easy dispensing of the contact lens solution into the retaining compartments.

It is yet another object of the present invention to provide a new and improved storage device for contact lens including a novel mechanism for generating streams of contact lens solution from a reservoir which flow to an exterior of the storage device and can be used to rinse and/or clean contact lenses.

It is still another object of the present invention to provide a new and improved storage device for contact lens including a novel mechanism for enabling contact lens retaining compartments to be filled with contact lens solution from an internal reservoir in the storage device.

In order to achieve these objects and others, a storage device for storing contact lenses and contact lens solution in accordance with the invention includes a case defining a reservoir for contact lens solution and a pair of contact lens retaining compartments for retaining contact lenses. The case includes a mechanism for causing a stream of contact lens solution to flow from the reservoir to an exterior of the case (for use when rinsing and/or cleaning the contact lens) and another mechanism for causing the contact lens solution to flow from the reservoir into the compartments (for use when storing the contact lenses in the compartments). These mechanisms can be alternatively enabled depending on the particular use sought for the contact lens solution.

The mechanism which causes the stream of contact lens solution to flow from the reservoir exterior of the case may include an exposed nipple which may be covered by a closure member when it is not desired to obtain contact lens solution and a flexible pressure application portion of the case which causes an increase in pressure in the reservoir when depressed. This increase in pressure causes the contact lens solution to flow out of the reservoir through an aperture in the nipple. The nipple may be removably attached to a projection formed on the case so that the reservoir can be refilled by detaching the nipple from the case and pouring contact lens solution through the projection. The nipple may be closed by a closure member removably attachable to the case when it is not desired to have a flow of contact lens solution therethrough, e.g., when it is desired to fill the compartments.

The mechanism for causing the contact lens solution to flow into the compartments may include a pair of valves each associated with a respective compartment. Preferably, the valves are constructed to provide a one-way flow of contact lens solution from the reservoir to the compartments and not in the reverse direction to avoid contamination of the contact lens solution in the reservoir. Each valve has an inlet opening situated in or communicating with the reservoir and an outlet opening. A flow path is formed in the case from the outlet opening of each valve to the respective compartment and includes a conduit in a mounting projection of a cover of the compartment. The covers are constructed such flow of contact lens solution through the conduits therein from the valves is enabled only when the covers are open. Accordingly, closing the covers presents flow of contact lens solution into the compartments.

Thus, when it is desired to fill the compartments, the closure member is attached to the case to block the aperture in the nipple and the covers are opened. When it is desired to obtain a stream of contact lens solution to clean or rinse a contact lens, the covers are closed and the closure member is detached form the case.

An embodiment of a storage device for storing contact lenses and contact lens solution is also possible wherein the mechanism for causing a stream of contact lens solution to flow exterior of the case is provided without the mechanism for causing the flow of contact lens solution into the compartments. In another embodiment, the mechanism for causing the flow of contact lens solution into the compartments is provided without the mechanism for causing a stream of contact lens solution to flow exterior of the case. That is, these two mechanisms can be independent of one another, and may also combined without types of contact lens solution dispensing mechanisms in a common case.

BRIEF DESCRIPTION OF THE DRAWINGS

The invention, together with further objects and advantages thereof, may best be understood by reference to the following description taken in conjunction with the accompanying drawings wherein like reference numerals identify the same or similar elements.

FIG. 6 is a cross-sectional view taken along the line 6-6 of FIG. 5.

FIG. 13 is a top view of the upper housing member of the combined contact lens case and solution storage device shown in FIG. 1.

FIG. 14 is a cross-sectional view of the upper housing member shown in FIG. 13 taken along the line 14-14 in FIG. 13.

FIG. 15 is a cross-sectional view of the upper housing member shown in FIG. 13 taken along the line 15-15 in FIG. 13.

FIG. 18 is a perspective view of the nipple of the combined contact lens case and solution storage device shown in FIG. 1.

FIG. 19 is a cross-sectional view of the nipple shown in FIG. 18 taken along the line 19-19.

FIG. 22 is a top view of the cover shown in FIG. 20.

FIG. 23 is a cross-sectional view of the cover shown in FIG. 20 taken along the line 23-23 in FIG. 22.

FIG. 24 is a side view of the cover shown in FIG. 20.

FIG. 25 is a cross-sectional view of the cover shown in FIG. 20 taken along the line 25-25 in FIG. 24.

FIG. 26 is a front view of a check valve of the combined contact lens case and solution storage device shown in FIG. 1.

FIG. 27 is a cross-sectional view of the check valve shown in FIG. 26 take along the line 27-27 of FIG. 26.

FIG. 28 is a top view of the check valve shown in FIG. 26.

FIG. 29 is a top view of a valve member of the combined contact lens case and solution storage device shown in FIG. 1.

FIG. 30 is a front view of the valve member shown in FIG. 29.

FIG. 34 is a perspective view of another embodiment of a combined contact lens case and solution storage device in accordance with the invention shown in an open state.

DETAILED DESCRIPTION OF THE INVENTION

Figure 1:
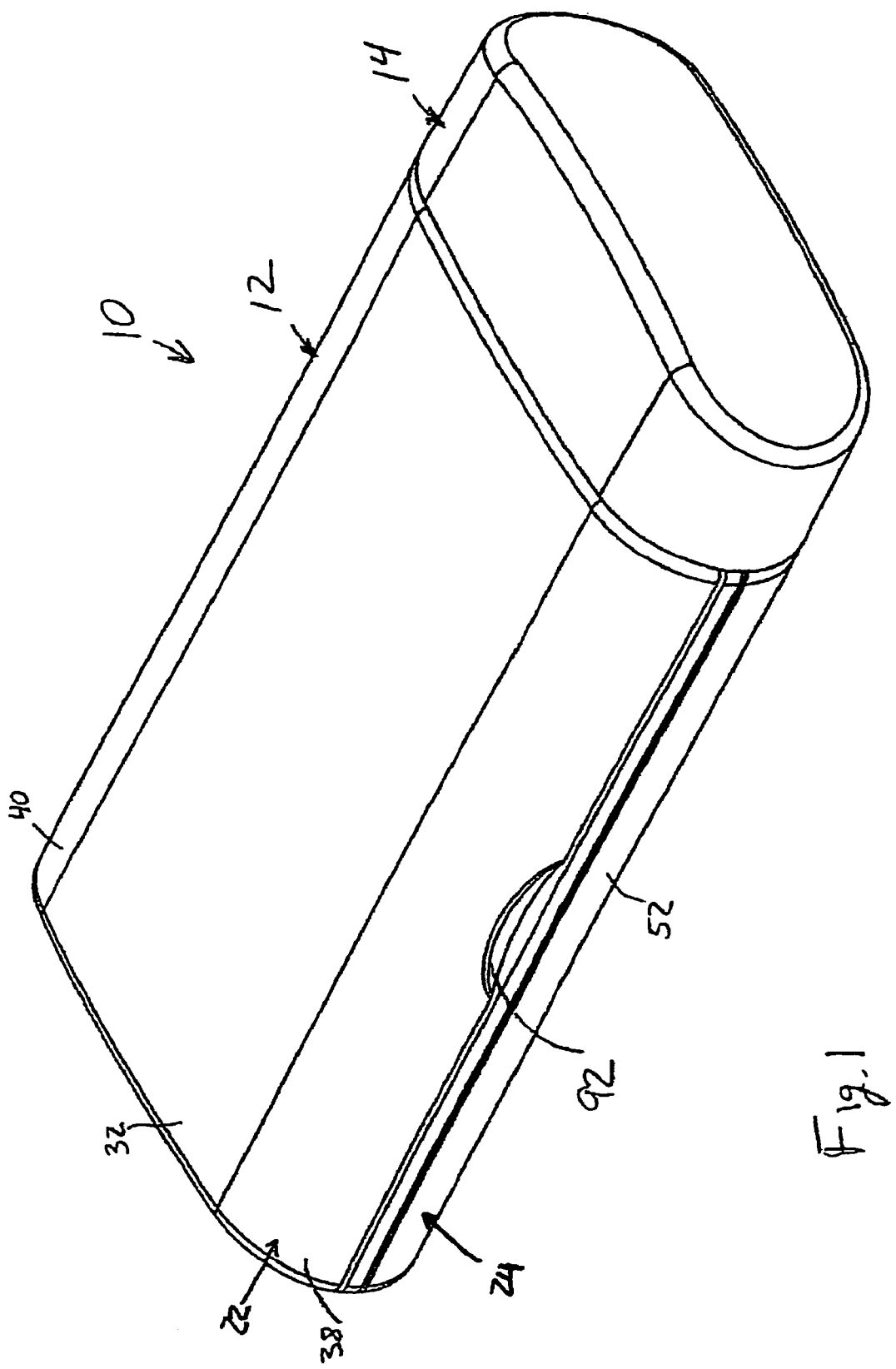
FIG. 1 is a perspective view of a combined contact lens case and solution storage device in accordance with the invention shown in a closed state.
Figure 2:
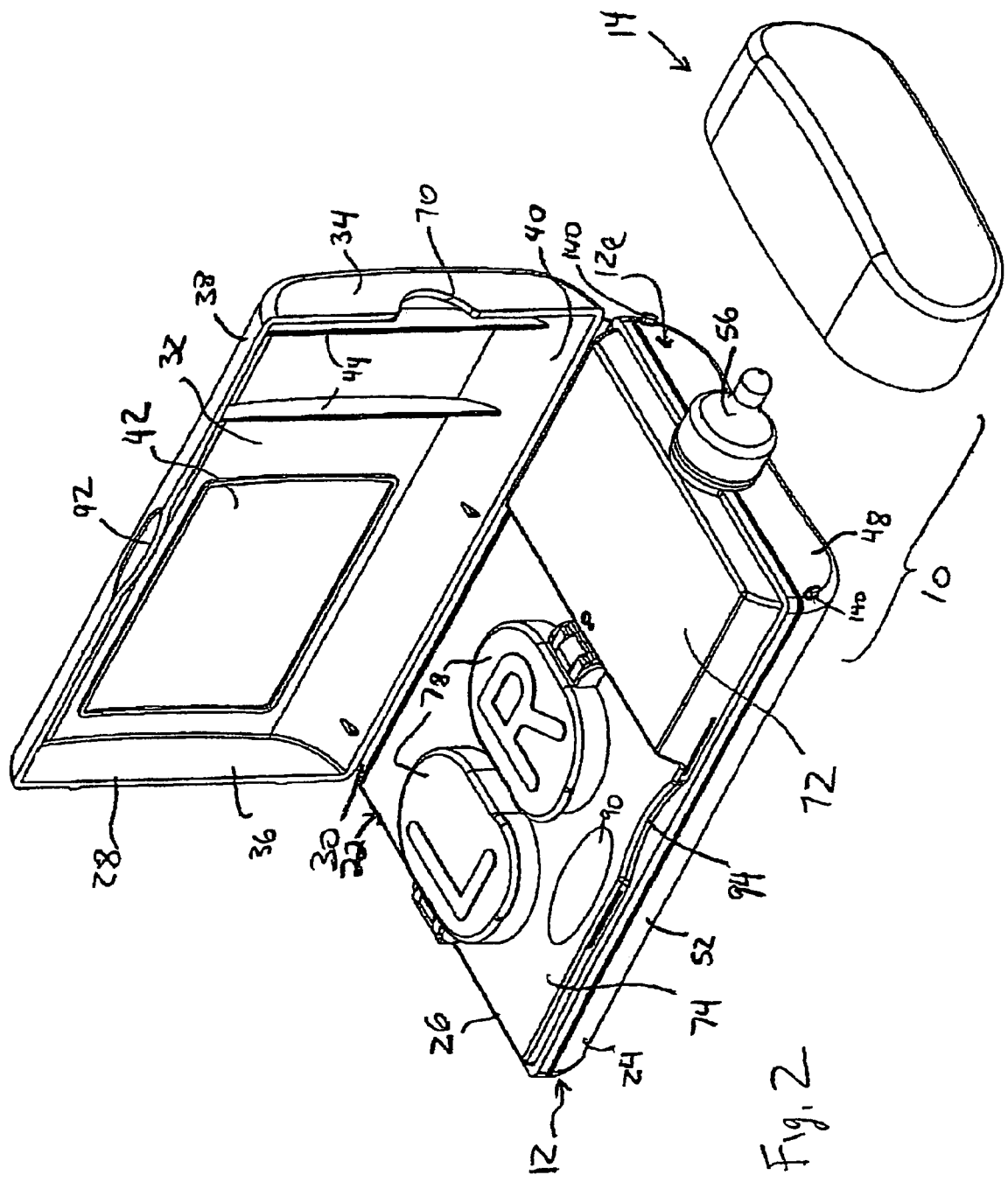
FIG. 2 is a perspective view of the combined contact lens case and solution storage device shown in FIG. 1 in position for use in rinsing or cleaning a contact lens.

Referring to the accompany drawings wherein like reference numerals refer to the same or similar elements, FIGS. 1-10 show a first embodiment of a combined contact lens and contact lens solution storage device 10 in accordance with the invention which includes a case 12 and an end cap 14 removably attachable to the case 12 at one side 12a thereof. The case 12 generally defines a refillable reservoir 16 in which contact lens solution can be stored and a pair of contact lens retaining compartments 18, 20, each receivable of one contact lens. The case 12 provides mechanisms for removing the contact lens solution from the reservoir 16 in two different ways, namely, by forcing the contact lens solution out of the reservoir 16 in the form of a stream which can be used to rinse and/or clean the contact lenses or by forcing the contact lens solution out of the reservoir 16 and into the compartments 18, 20. The latter is used when the contact lenses are being stored, e.g., overnight.

More specifically, the case 12 includes an upper housing member 22 and a lower housing member 24 attached to the upper housing member 22, for example by hot plate welding. The reservoir 16 is defined between the upper and lower housing members 22, 24. The end cap 14 and the upper and lower housing members 22, 24 may all be formed of plastic, such as polypropylene.

Referring specifically to FIGS. 11-15, upper housing member 22 includes a reservoir covering section 26 which is attached to the lower housing member 24 to form the reservoir 16 therebetween and a cover section 28 pivotally connected to the reservoir covering section 26, e.g., by a living hinge 30. The upper housing member 22 includes any conventional structure to enable the cover section 28 to be pivoted about the hinge 30 to snap into place on the reservoir covering section 26. The cover section 28 includes a substantially planar upper wall 32, opposed, substantially planar side walls 34, 36 and opposed, arcuate front and rear walls 38, 40 which are contiguous with the upper wall 32 (see FIGS. 11 and 12). A mirror 42 is attached to a portion of the upper wall 32 which will cover the compartments 18, 20 when the cover section 28 is closed. Supporting ribs 44 are optionally formed alongside the mirror 42 extending downward from the upper wall 32.

Figure 16:
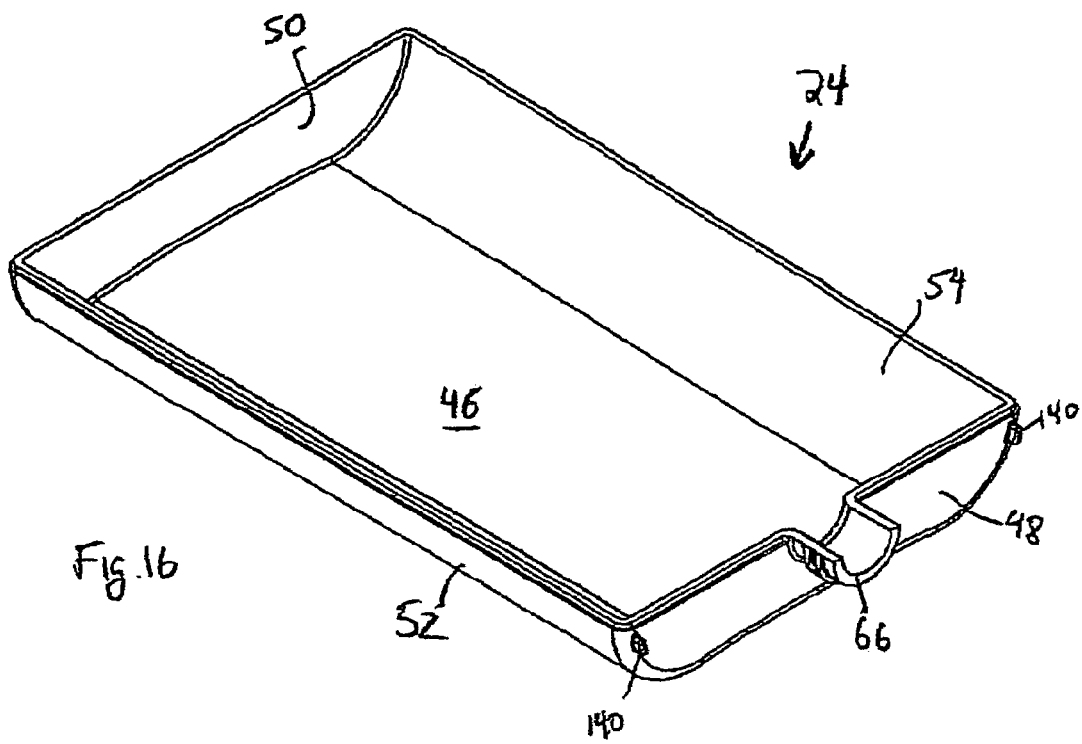
FIG. 16 is a perspective view of the lower housing member of the combined contact lens case and solution storage device shown in FIG. 1.
Figure 17:
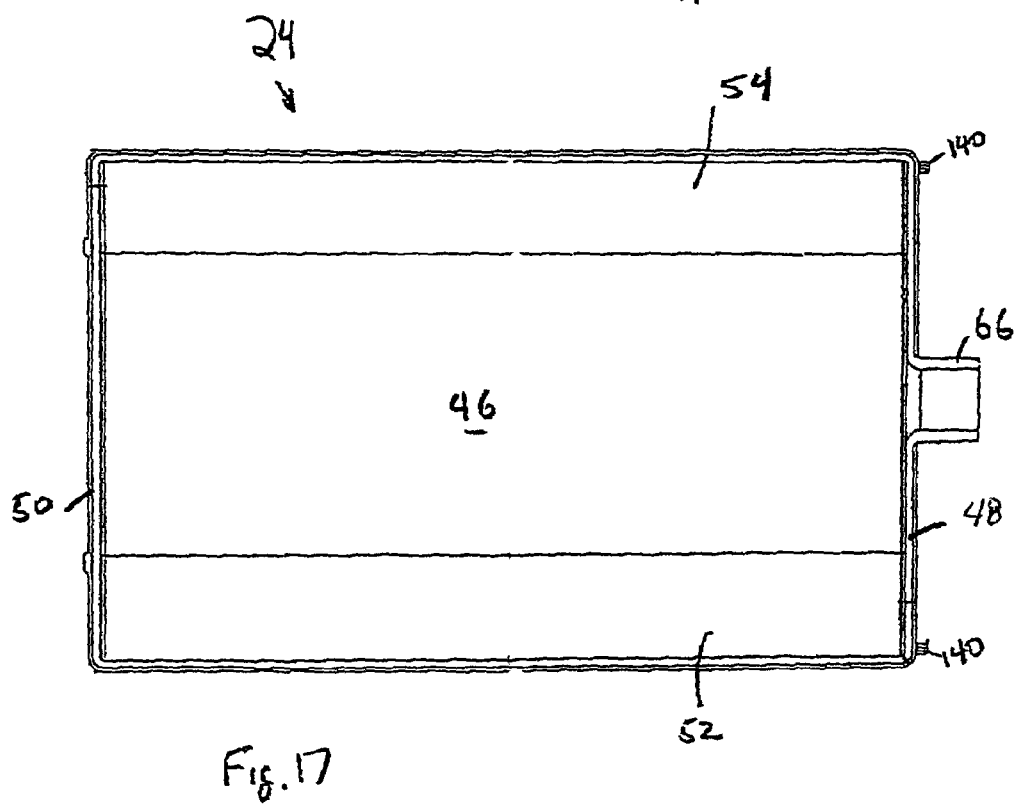
FIG. 17 is a top plan view of the lower housing member of the combined contact lens case and solution storage device shown in FIG. 1.
Figure 20:
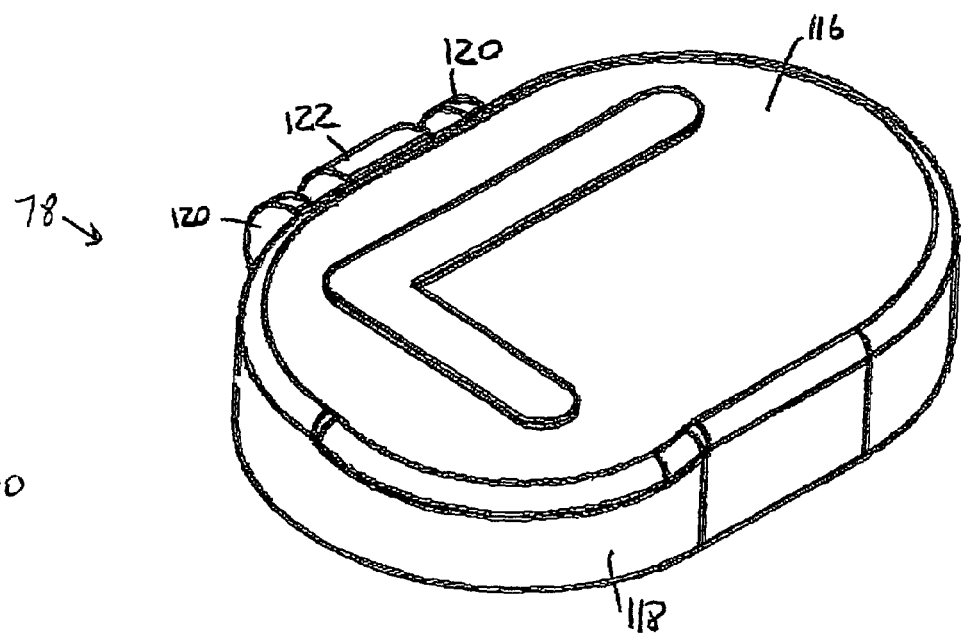
FIG. 20 is a perspective view of a cover of the combined contact lens case and solution storage device shown in FIG. 1.
Figure 21:
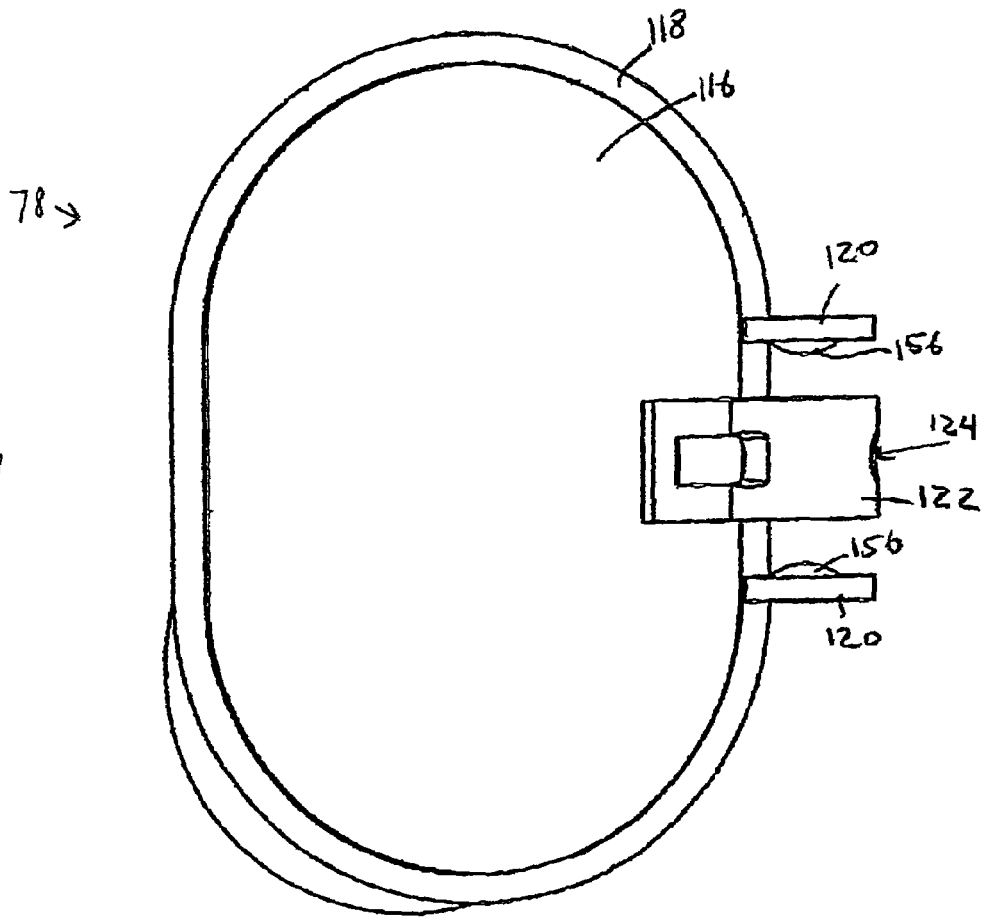
FIG. 21 is a bottom view of the cover shown in FIG. 20.
Figure 31:
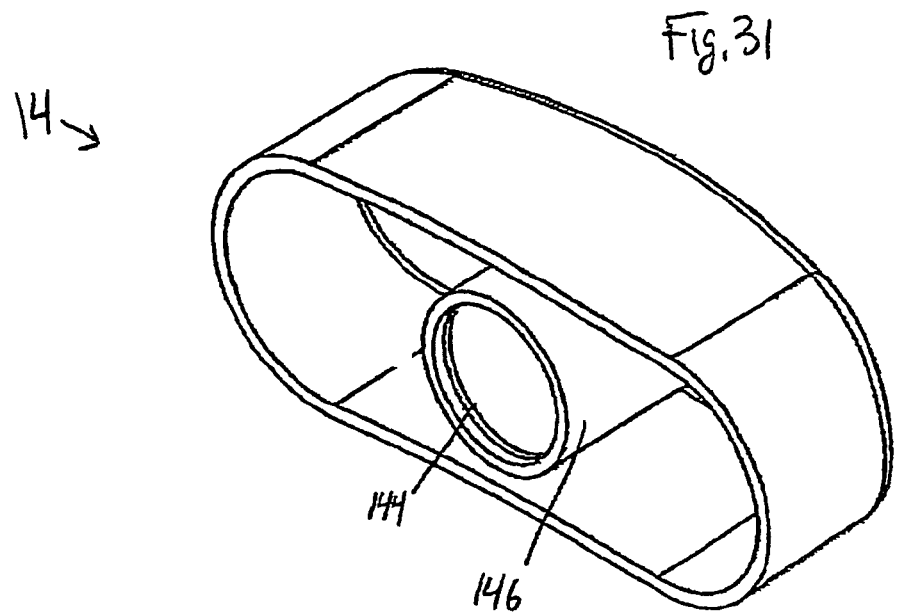
FIG. 31 is a perspective view of an end cap of the combined contact lens case and solution storage device shown in FIG. 1.
Figure 32:
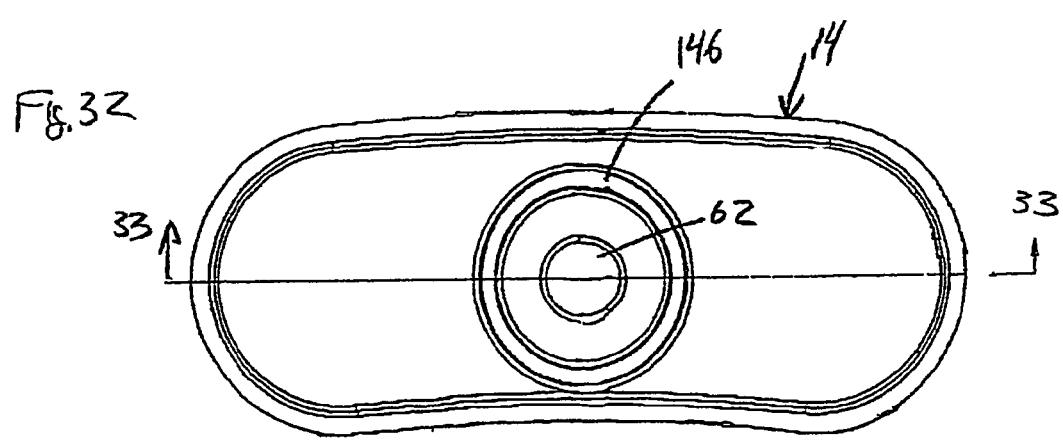
FIG. 32 is a rear view of the end cap shown in FIG. 31.

Lower housing member 24 has a bottom wall 46, opposed, substantially planar side walls 48, 50 and opposed, arcuate front and rear walls 52, 54 which are contiguous with the bottom wall 46 (see FIGS. 16 and 17). Front and rear walls 52, 54 curved upward from the bottom wall 46, which may be planar or have a slightly curvature in order to provide the case 12 with a curving form. The bottom wall, front and rear walls 46, 52, 54 define support points which contact an underlying support structure when the contact lens device 10 is resting thereon. The lower housing member 24 can have a different shape than that shown in the drawings and described above, but at a minimum, should include one or more walls which define part of the reservoir 16 and is capable of receiving a fluid, i.e., contact lens solution.

The mechanism for forcing the contact lens solution out of the reservoir 16 in the form of a stream includes a flow nipple 56 removably attached to the upper and lower housing members 22, 24. Nipple 56 has an aperture 58 at a tip 60 through which streams of contact lens solution stored in the reservoir 16 can flow to an exterior of the case 12, when the end cap 14 is apart from the case 12 (see FIGS. 18 and 19). When the end cap 14 is attached to the case 12, an engagement pad 62 arranged on a side wall of the end cap 14 contacts the tip 60 and covers the aperture 58 so that the contact lens solution cannot flow through the aperture 58. Removal of the end cap 14 from engagement with the case 12 therefore allows flow of the contact lens solution from the reservoir 16. The nipple 56 may be formed of plastic, such as polypropylene.

To allow for attachment and detachment of the nipple 56 from the base 12, the upper housing member 22 and the side wall 48 of the lower housing member 24 each includes an outwardly directed, semi-cylindrical threaded projection 64, 66 which align with each other to form a cylindrical threaded projection onto which the nipple 56 is threaded (see FIG. 6). The inner surface of a tubular portion of the dispensing nipple 56 is threaded (see FIG. 19) and thus can be rotated onto and apart from the cylindrical threaded projection. To refill the reservoir 16, the nipple 56 is rotated apart from the cylindrical threaded projection and contact lens solution is poured into the reservoir 16 through the cylindrical threaded projection.

Figure 11:
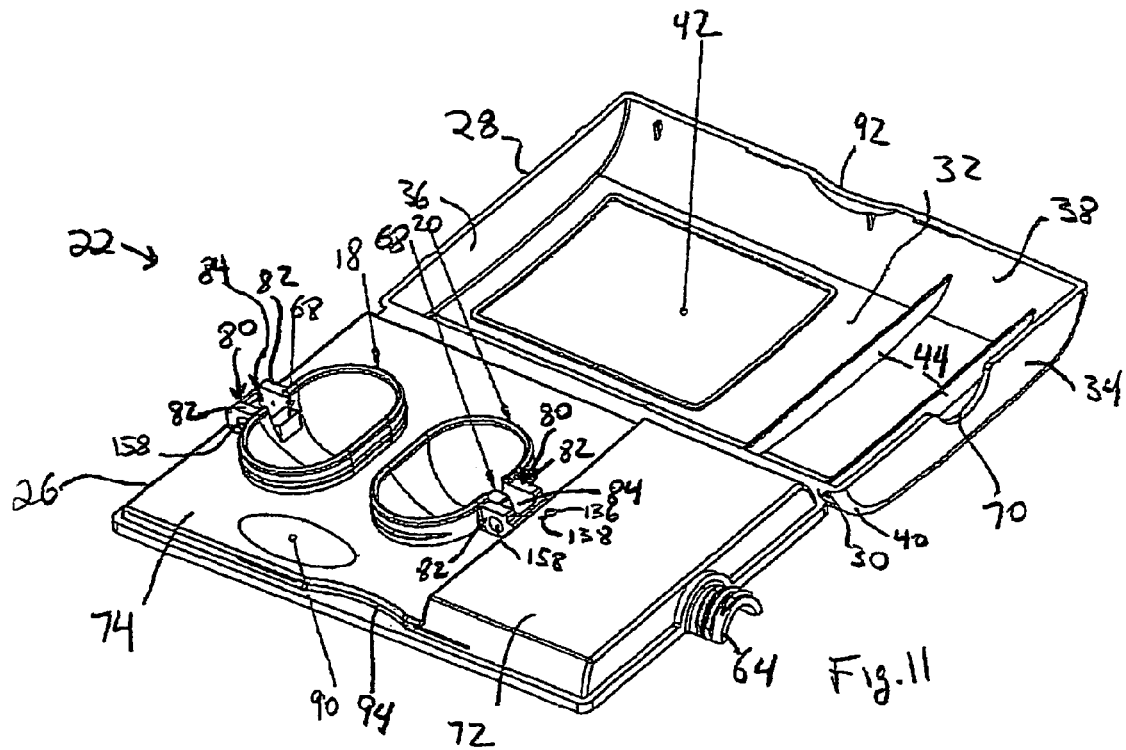
FIG. 11 is a top perspective view of the upper housing member of the combined contact lens case and solution storage device shown in FIG. 1.
Figure 12:
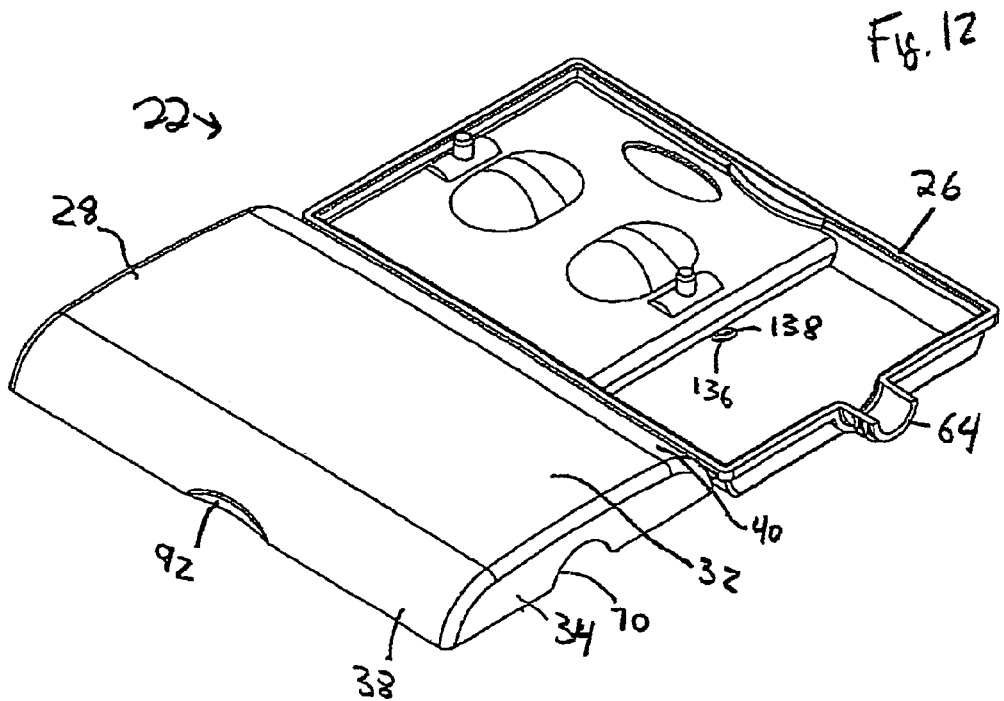
FIG. 12 is a top perspective view of the upper housing member of the combined contact lens case and solution storage device shown in FIG. 1.

To enable the cover section 28 to close onto the reservoir covering section 26 of the upper housing member 22 in view of the presence of the nipple 26, the side wall 34 of the covering section 28 of the upper housing member 22 includes a semi-circular indentation 70 (see FIGS. 11 and 12).

In addition to the nipple 56, the mechanism for forcing the contact lens solution out of the reservoir 16 in the form of a stream includes the formation of a pressure application portion 72 on the reservoir covering section 26 of the upper housing member 24, preferably proximate the nipple 56. The pressure application portion 72 is flexible and can be depressed toward the lower housing member 24 and when pressure is removed, it returns to its original shape. The pressure application portion 72 is in the form of an elevated platform raised above the level of a remaining portion of the reservoir covering section 26.

The flow of contact lens solution from the reservoir 16 through the nipple 56 is thus obtained by applying pressure to the pressure application portion 72 to cause an increase in pressure in the reservoir 16 which, when the end cap 14 is apart from the base 12, causes contact lens solution to flow from the reservoir 16 out through the aperture 58 in the nipple 56. If the pressure application portion 72 is continuously pressed, a continuous stream of contact lens solution will flow through the aperture 58 in the nipple 56. On the other hand, if pressure is applied intermittently to the pressure application portion 72, multiple streams of contact lens solution will flow through the aperture 58 in the nipple 56.

Referring to FIG. 11, the reservoir covering section 26 of the upper housing member 22 includes a support portion 74 defining the contact lens retaining compartments 18, 20 (one for the left contact lens and one for the right contact lens) and the pressure application portion 72 alongside the support portion 74. Each compartment 18, 20 may be defined by arcuate surfaces adapted to retain contact lens storage solution and a contact lens. Any form and shape of depression can also be used to define the compartments 18, 20.

Figure 3:
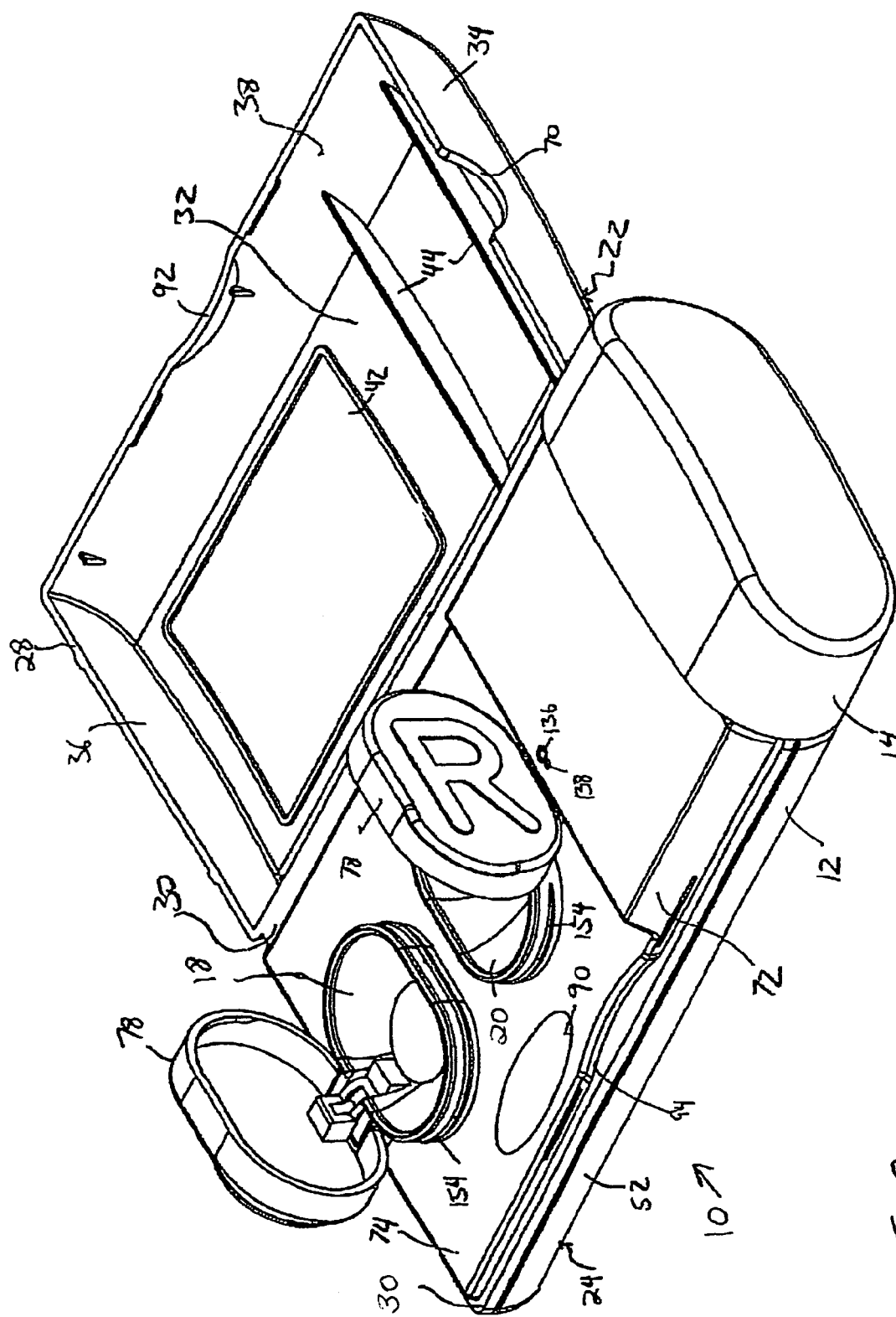
FIG. 3 is a perspective view of the combined contact lens case and solution storage device shown in FIG. 1 in position for accessing the contact lens retaining compartments.
Figure 4:
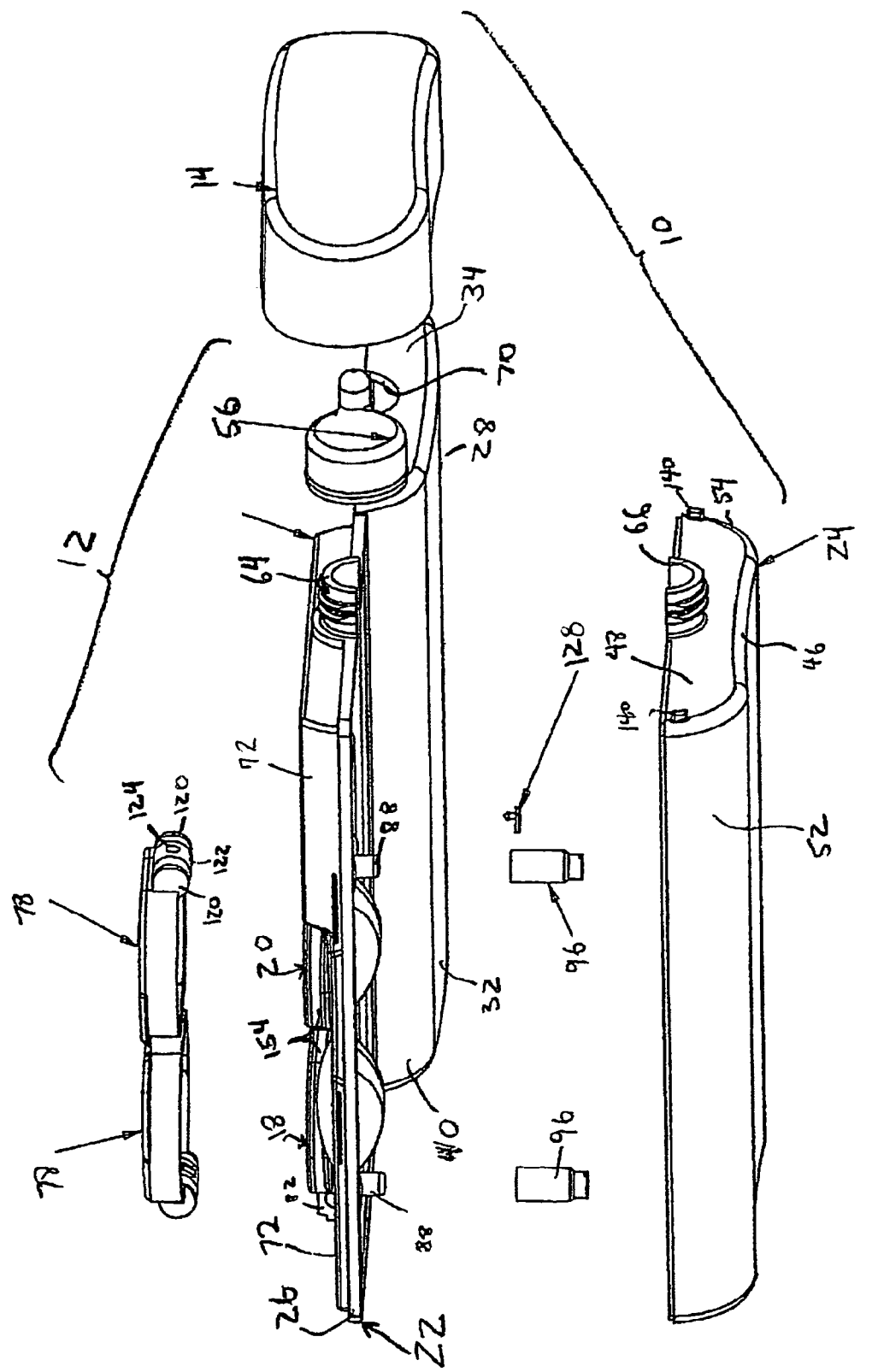
FIG. 4 is an exploded view of the combined contact lens case and solution storage device shown in FIG. 1.
Figure 10:
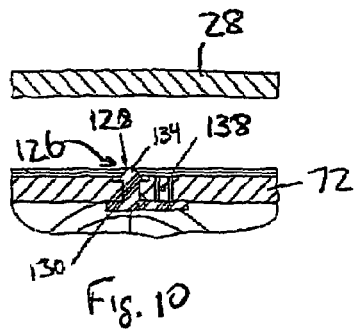
FIG. 10 is an enlarged view of the section designated 10 in FIG. 9.
Figure 9:
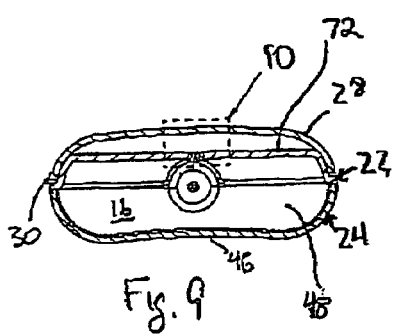
FIG. 9 is a cross-sectional view taken along the line 9-9 of FIG. 7.
Figure 5:
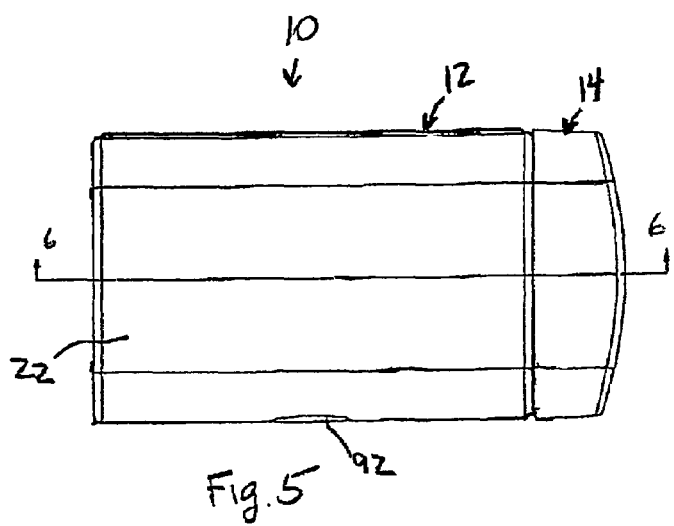
FIG. 5 is a top view of the combined contact lens case and solution storage device shown in FIG. 1.
Figure 8:
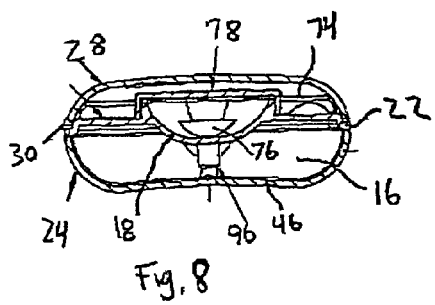
FIG. 8 is a cross-sectional view taken along the line 8-8 of FIG. 7.
Figure 7:
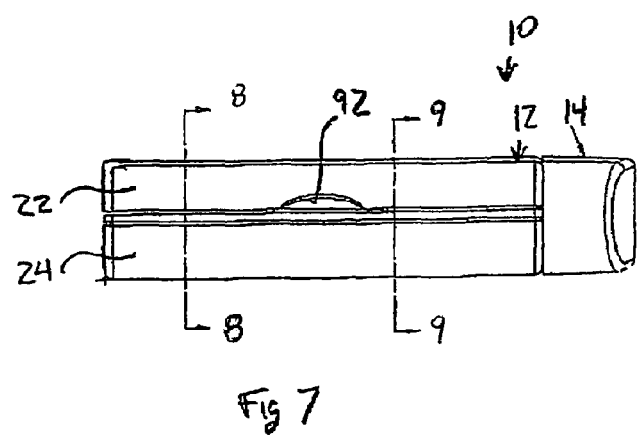
FIG. 7 is a side view of the combined contact lens case and solution storage device shown in FIG. 1.

As shown in FIG. 3, covers 78 are pivotally connected to the support portion 74 of the upper housing member 22 to selectively cover the compartments 18, 20. When cover section 28 is in its open condition shown in FIGS. 2 and 3, the covers 78 can be opened to access the compartments 18, 20 to place contact lenses 76 therein or retrieve contact lenses therefrom. One or both of the covers 78 preferably includes an indication of which contact lens is retained therein, e.g., the covers 78 include the letter "R" or "L" as shown.

Support portion 74 also includes an integral mounting bracket 80 alongside each compartment 18, 20 for mounting one of the covers 78 thereto (see FIGS. 13-15). Each mounting bracket 80 includes a pair of projections 82 separated by a semi-cylindrical cavity 84 which is separated from the compartments 18, 20 by a ledge 68. An aperture 86 is formed at a bottom of the cavity 84 between each pair of projections 82 and leads to a vertical channel 88 (see FIGS. 14 and 15). A demarcated pressure application zone 90 is formed in front of the compartments 18, 20, e.g., by reducing the thickness of the support portion 74 to create an easily depressible zone which can be pushed inward toward the lower housing member 22 relative to other portions of the support portion 74. The purpose of the cavities 84, channels 88 and pressure application zone 90 are discussed below.

To facilitate opening of the cover section 28 from its closed position shown in FIG. 1, a notch 92 may be formed in the front wall 38 of the cover section 28 in alignment with a notch 94 in the support section 74. The notches 92, 94 enable a user to insert a fingernail to pry the case 12 open by exerting pressure to separate the cover section 28 from the reservoir covering section 26.

The mechanism for forcing the contact lens solution out of the reservoir 16 and into the compartments 18, 20 includes check valves 96 arranged in the reservoir 16 and engaged with the channel 88 (see FIG. 6). Check valves 96 each provide a one-way flow of contact lens solution from the reservoir 16 into an associated one of the channels 88.

To provide the one-way flow of contact lens solution, i.e., to allow the contact lens solution to flow from the reservoir 16 into the channels 88 but not from the channels 88 into the reservoir 16 (which is necessary to avoid contamination of the remaining contact lens solution in the reservoir 16), each check valve 96 includes a tubular member 98 having a plurality of protuberances 100 formed on an inner surface and including a lower chamber 102 formed at a bottom of the tubular member 98, a pumping chamber 104 formed above the lower chamber 102, a shoulder 106 formed between the lower chamber 102 and the pumping chamber 104 and an upper chamber 108 (see FIGS. 26-28). The upper chamber 108 receives the channel 88 and defines an outlet opening of the tubular member 98.

A movable mass, such as a ball 110, rests on the shoulder 106 in the absence of an upward flow of contact lens solution through the valve 96 (the cause of which is discussed above). Thus, the downward flow of contact lens solution from the upper chamber 108 would urge the ball 110 against the shoulder 106 and prevent flow into the lower chamber 102. A one-way flow of contact lens solution through the valves 96 is thereby provided. Other constructions of one-way valves are also envisioned within the scope and spirit of the invention.

A lower, annular surface 112 of the tubular member 98 is provided with an inlet opening in the form of one or more notches or cut-outs 114 so that the lower chamber 102 is in communication with the reservoir 16 and contact lens solution from the reservoir 16 can flow into the lower chamber 102 therethrough (see FIG. 27). For example, six notches 114 can be formed in the tubular member 98 spaced equi-angularly about the lower annular surface 112. The lower surface 112 of the tubular member 98 is in contact with or very proximate to the inner surface of the bottom wall 46 of the lower housing member 24 so that the contact lens solution flows through the notches 114.

The presence of the protuberances 100 formed on the inner wall of the tubular member 98 and which separate the pumping chamber 104 from the upper chamber 108 limits the upward movement of the ball 110 in the pumping chamber 104. The ball 110 cannot pass from the pumping chamber 104 to the upper chamber 108 through the protuberances 100. Each protuberance 100 may be formed with a flat surface or arcuate surface angled upward and inward from the inner wall such that the cross-sectional area of the pumping chamber 104 gradually decreases in the upward direction at the location of the protuberances 100. The ball 110 can be placed into the pumping chamber 104 by forcing it through the opening defined by the lower chamber 102 or between the protuberances 110.

Tubular member 98 may be formed of a flexible material such as rubber. The mass or ball 110 is preferably formed of a rigid material such as a metal.

Covers 78 each include a planar portion 116, a rim 118 extending downward from an outer edge of the planar portion 116, a pair of mounting flanges 120 along one side of the planar portion 116 and a projection 122 arranged between the mounting flanges 120 and defining a conduit 124 therein (see FIGS. 20-25). The rim 118 is designed to frictionally engage with a projection 154 formed on the support portion 74 and defining each compartment 18, 20. Each projection 82 of the mounting brackets 80 fits between the projection 122 and a respective one of the mounting flanges 118 to pivotally attach the covers 78 to the upper housing member 22. A side projection 156 may be formed in an inner surface of each mounting flange 118 (see FIGS. 22 and 25) to engage with a corresponding depression 158 in the projections 82 (see FIG. 11) to provide for pivotal movement of the cover 78 relative to the projection 82. The projection 122 fits in the cavity 84 and rotates therein (see FIG. 6). The conduit 124 is designed to be oriented in a direction roughly parallel to the planar portion 116 so that when the cover 78 is closed, the conduit 124 is not in communication with the channel 88 (i.e., the projection 122 blocks the channel 88 as shown in FIG. 6) but when the cover 78 is open, the conduit 124 communicates with the channel 88. Thus, when the cover 78 is closed, flow of contact lens solution into the cavity 84 of the upper housing member 22 is prevented.

The flow of contact lens solution from the reservoir 16 into the compartments 18, 20 is created, when the covers 78 are in an open position, by depressing the pressure application zone 90 on the support portion 74 which causes an increase in pressure in the reservoir 16. As a result of this pressure increase, contact lens solution in the reservoir 16 is forced through the notches 114 in each tubular member 98 upward into the lower chambers 102 of the tubular members 98 and pushes the ball 110 in the pumping chambers 104 upward and apart from the shoulder 106 (the upward movement of the ball 110 being limited by the protuberances 100). A flow path is thereby opened between the ball 110 and the shoulder 106 through which the contact lens solution flows into the upper chambers 108. Since the channels 88 are received in the upper chambers 108, the contact lens solution flows into the channel 88. From the channels 88, the contact lens solution flows through the respective aperture 86 into the respective conduit 124 in the open cover 78 and from the conduit 124 over the ledge 68 into the respective compartment 18, 20.

However, this flow is restricted to when the covers 78 are in an open position because the covers 78 are designed to allow a flow of contact lens solution from the reservoir 16 through the cavities 84 and into the compartments 18, 20 only when the covers 78 are in an open position. When the covers 78 close the compartments 18, 20, the contact lens solution cannot flow from the reservoir 16 therein. This enables a selective flow of contact lens solution to be obtained. That is, by a specific positioning of the end cap 14 and covers 78, the contact lens solution can either be directed into the compartments 18, 20 or through the nozzle 56. To direct the contact lens solution into the compartments 18, 20, the covers 78 are opened and the end cap 14 is attached to the case 12. To obtain a stream of contact lens solution through the nozzle 56, the covers 78 are closed and the end cap 14 is detached from the case 12.

Upon removal of contact lens solution from the reservoir 16, air must be supplied into the reservoir to maintain the operability of the device 10. Nevertheless, it must be ensured that contact lens solution does not flow out of the reservoir 16 through whatever means are provided to allow intake air into the reservoir 16. To this end, a valve mechanism 126 is arranged in the case 12 and specifically in the pressure application portion 72 of the reservoir covering section 26 of the upper housing member 22 (see FIG. 10). The valve mechanism 126 includes a valve member 128 having a planar portion 130 and a projection 132 with an enlarged tip 134 (see FIGS. 29 and 30). An aperture 136 is formed in the pressure application portion 72 and the projection 132 is situated in the aperture 136 with the tip 134 extending through the aperture 136 (see FIG. 10). An intake aperture 138 is also formed alongside aperture 136 and at an internal side, the planar portion 130 of the valve member 128 covers the intake aperture 138. Alternatively, the aperture 136 could also constitute an intake aperture provided it is constructed to hold the valve member 128 in place.

The valve mechanism 126 is effective to allow air intake through intake aperture 138 when the pressure in the reservoir 16 is less than the pressure in the ambient atmosphere. The pressure differential causes the planar portion 130 to move apart from the intake aperture 138 and allow air flow into the reservoir 16. On the other hand, when pressure application portion 72 and pressure application zone 90 are depressed, the contact lens solution flows against the planar portion 130 to maintain the closure of the intake aperture 138 and prevent outflow of contact lens solution therethrough.

Figure 33:
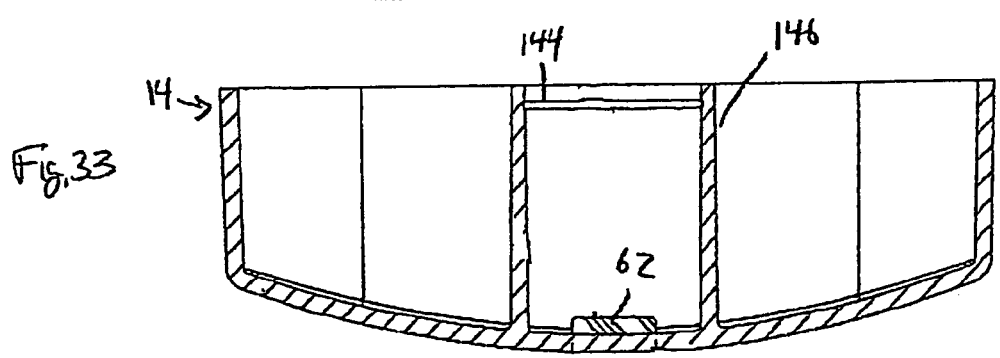
FIG. 33 is a cross-sectional view of the end cap shown in FIG. 31 take along the line 33-33 of FIG. 32.
Figure 3A:
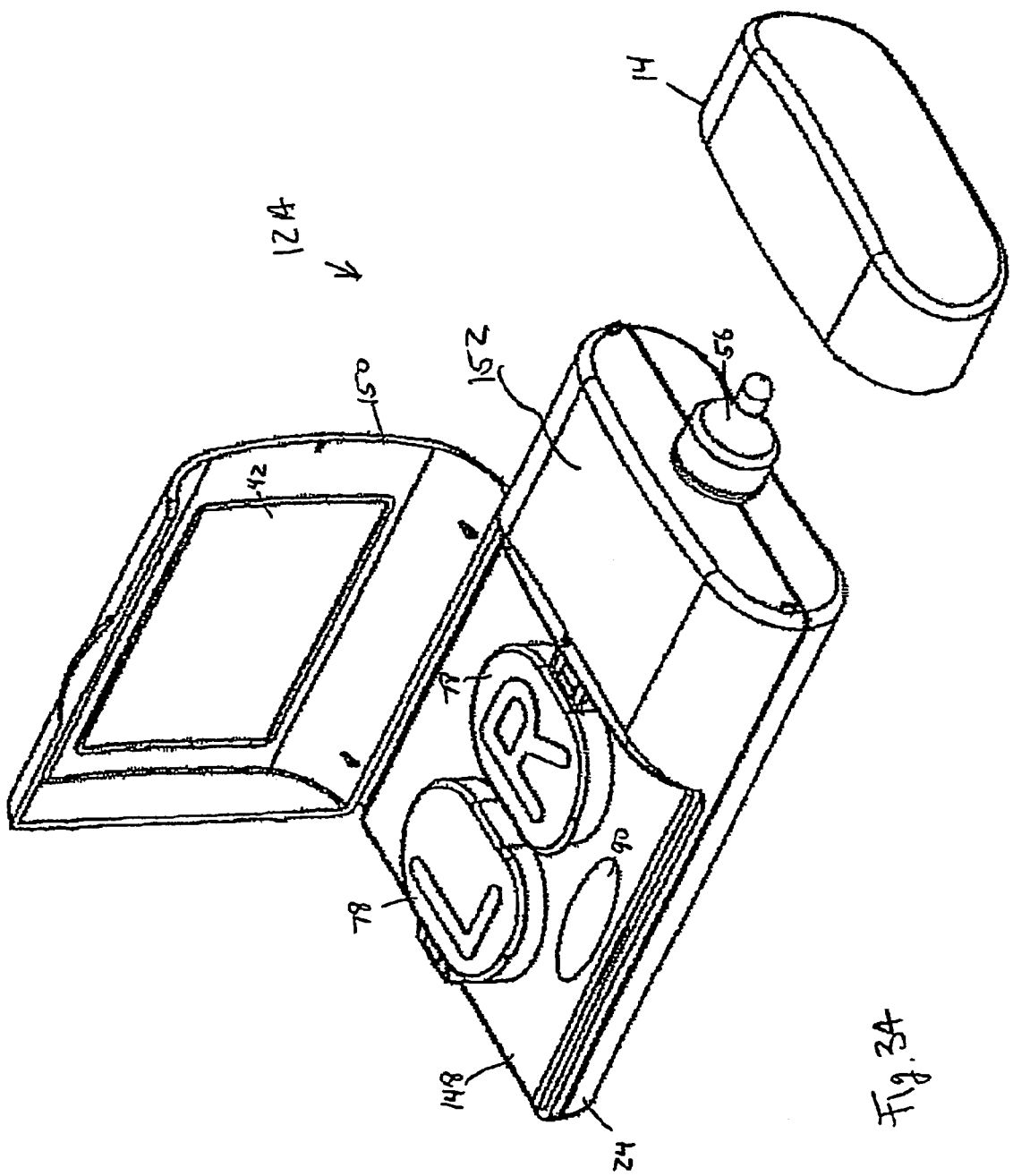

To expose the aperture 58 of the nipple 56 and enable the contact lens solution to be dispensed from the reservoir 16 therethrough, the end cap 14 is removably attached to the case 12. This attachment may be achieved by forming projections 140 on the side wall 48 of the lower housing member 22 (see FIGS. 16 and 17). The projections 140 create a friction fit between the end cap 14 and the case 12 so that the end cap 14 can be attached securely to the case 12 and is detachable therefrom only by applying pressure to pull the end cap 14 away from the case 12. In addition, the nipple 56 is provided with a snap rib 142 which engages with an annular groove 144 formed in an inner surface of a tubular inner projection 146 on the end cap 14 to thereby provide an additional measure of engagement between the end cap 14 and the case 12 (see FIGS. 6, 19 and 33). The tubular projection 146 is designed to substantially enclose the nipple 56 when the end cap 14 is attached to the case 12. Either or both of the attachment mechanisms, i.e., the projections 140 or the cooperating snap rib 146 and annular groove 144, may be provided.

Other mechanisms for removably attaching the end cap 14 to the case 12 are also envisioned within the scope and spirit of the invention.

In the illustrated embodiment, the covers 78 are mounted along a side edge to the upper housing member 22. It is also envisioned that the covers 78 may be mounted along either their top or bottom edge to the upper housing member 22. Regardless of which edge of the covers 78 is mounted to the upper housing member 22, since the flow of contact lens solution from the reservoir 16 into the compartments 18, 20 passes through the mounting structure, it is desirable that the mounting structure and pressure application zone 90 should be proximate one another. This would help assure that depressing the pressure application zone 90 causes an adequate flow of contact lens solution through the check valves 96 into the compartments 18, 20. Thus, an alternative design configuration is possible wherein the covers 78 are mounted at their top edges to the upper housing member 22 and the position of the pressure application zone 90 is altered from that shown to be proximate the top edge of the covers 78.

In addition, in the illustrated embodiment, since the covering section 28 of the upper housing member 22 covers the pressure application portion 72 of the reservoir covering section 26 when the case 12 is closed, it is not possible to obtain a stream of contact lens solution from the reservoir 16 through the nipple 56 when the case 12 is closed. In an alternative case 12A shown in FIG. 34 (wherein the same reference numerals are used to designate the same or similar parts), an upper housing member 148 is designed with a covering section 150 which extends over only the support portion 74 and a pressure application portion 152 which defines an outer periphery of the case 12. In this manner, the pressure application portion 152 is not covered by the covering section 150 and it becomes possible to obtain a stream of contact lens solution from the reservoir 16 even when the covering section 150 is closed.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

We claim:

1. A storage device for storing contact lenses and contact lens solution, comprising:
    a case defining a reservoir for contact lens solution and a pair of contact lens retaining compartments for retaining contact lenses, said case including stream generating means for causing a stream of contact lens solution to flow from said reservoir to an exterior of said case and filling means for causing the contact lens solution to flow from said reservoir into said compartments,
        wherein said case includes an upper housing member defining said compartments and a lower housing member attached to said upper housing member, said reservoir being defined between said upper and lower housing members,
        wherein said upper housing member includes a reservoir covering section attached to said lower housing member to form said reservoir therebetween and a cover section pivotally connected to the reservoir covering section, said compartments being defined in said reservoir covering section
        wherein said reservoir covering section includes a support portion defining said compartments and a flexible pressure application portion which causes an increase in pressure in said reservoir when depressed; and
    closure means removably attachable to said case for covering an exposed portion of said stream generating means through which the stream of contact lens solution flows.

2. The storage device of claim 1, wherein said case further includes a mirror arranged on an inner wall of said cover section.

3. The storage device of claim 1, wherein said case further comprises covers pivotally connected to said reservoir covering section to selectively cover said compartments.

4. The storage device of claim 3, wherein said reservoir covering section includes a mounting bracket alongside each of said compartment for mounting said covers, each of said mounting brackets including a pair of projections separated by a cavity communicating with a respective one of said compartments with an aperture being formed at a bottom of each of said cavities, said reservoir covering section further including a channel communicating with each of said apertures and a pressure application zone.

5. The storage device of claim 4, wherein said filling means comprise a pair of valves each associated with a respective one of said compartments, each of said valves having an inlet opening situated in said reservoir and an outlet opening, each of said channels being arranged in the outlet opening of a respective one of said valves.

6. The storage device of claim 5, wherein each of said valves includes a tubular member defining a lower chamber in communication with said reservoir, a pumping chamber above said lower chamber and a shoulder between said lower chamber and said pumping chamber, a mass resting on said shoulder and movable in said pumping chamber apart from said shoulder and limiting means for limiting movement of said mass in said pumping chamber apart from said shoulder whereby depression of said pressure application zone causes fluid in said reservoir to flow against said mass causing said mass to separate from said shoulder and open a passage between said lower chamber and said pumping chamber and flow through said passage toward said outlet opening and into said channel.

7. The storage device of claim 6, wherein said limiting means comprise a plurality of protuberances formed in an inner wall of said tubular member.

8. The storage device of claim 7, wherein said tubular member includes notches formed in an annular lower surface to enable flow communication between said lower chamber and said reservoir.

9. The storage device of claim 4, wherein a part of each of said covers is arranged in a respective one of said cavities and is pivotable to block said channels when in a closed position and allow flow through said cavities when in an open position.

10. The storage device of claim 9, wherein said covers each include a projection defining a conduit therein and arranged in the respective one of said cavities, said conduit being arranged to block said channel when said cover is closed and be in communication with said channel when said cover is open.

11. The storage device of claim 1, wherein said closure means comprise means for preventing flow of contact lens solution from said reservoir when said closure means are attached to said case.

12. The storage device of claim 1, wherein said exposed portion of said stream generating means comprise a flow nipple arranged on said case, said nipple having a tip with an aperture formed therein through which streams of contact lens solution stored in said reservoir flow to an exterior of said case when said closure means are detached from said case.

13. The storage device of claim 12, wherein said nipple is detachable from said case to enable refilling of said reservoir.

14. The storage device of claim 12, wherein said case includes a projection with threads and said nipple has corresponding threads arranged to engage with said threads of said projection.

15. The storage device of claim 12, wherein said closure means comprise a cap removably attachable to said case.

16. The storage device of claim 15, further comprising attachment means for removably attaching said cap to said case, said attachment means comprising an annular rib formed on an outer surface of said nipple and an annular groove formed on said cap and receivable of said annular rib of said nipple when said cap is attached to said case.

17. The storage device of claim 16, wherein said cap includes an interior cylindrical wall arranged to surround said nipple, said annular groove being formed on an inner surface of said cylindrical wall.

18. The storage device of claim 12, wherein said closure means comprise an engagement pad arranged to contact said tip and cover said aperture in said nipple when said closure means is attached to said case and thereby prevent flow of fluid from said reservoir through said aperture when said closure means is attached to said case.

19. The storage device of claim 12, wherein said stream generating means further comprise a pressure application zone formed on said case and arranged to cause an increase in pressure in said reservoir, said pressure application zone constituting a portion of said case having a reduced thickness in comparison to a surrounding portion of said case whereby application of pressure to said pressure application zone causes an increase in pressure in said reservoir and outflow of contact lens solution from said reservoir when said aperture in said nipple is uncovered.

20. The storage device of claim 1, wherein said filling means are constructed to provide a one-way flow of contact lens solution from said reservoir to said compartments and thereby prevent flow of contact lens solution from said compartments into said reservoir.

21. The storage device of claim 1, wherein said case further comprises a valve arranged to allow inflow of air into said reservoir and prevent outflow of contact lens solution from said reservoir.

22. The storage device of claim 21, wherein said valve comprises a valve member attached to said case, said case including an intake aperture, said valve member being arranged to cover said aperture upon application of pressure from said reservoir and separate from said aperture in the absence of pressure being applied from said reservoir.

23. A storage device for storing contact lenses and contact lens solution, comprising:
  a case defining a reservoir for contact lens solution and a pair of contact lens retaining compartments for retaining contact lenses, said case including
  a support portion on which said compartments are defined, said support portion including a cavity communicating with each of said compartments and having an aperture formed at a bottom thereof, a channel communicating with each of said apertures and a pressure application zone,
  wherein said support portion includes a mounting bracket alongside each of said compartments for mounting said covers, each of said mounting brackets including a pair of projections, said cavities being arranged between said projections,
  covers movably connected to said support portion to selectively cover said compartments, a part of each of said covers being arranged in a respective one of said cavities and being movable to block said channel when in a closed position and allow flow through said cavity when in an open position, and
  a pair of valves each associated with a respective one of said compartments, each of said valves having an inlet opening situated in said reservoir and an outlet opening, each of said channels being arranged in the outlet opening of a respective one of said valves,
  wherein each of said valves includes a tubular member defining a lower chamber in communication with said reservoir, a pumping chamber above said lower chamber and a shoulder between said lower chamber and said pumping chamber, a mass resting on said shoulder and movable in said pumping chamber apart from said shoulder and limiting means for limiting movement of said mass in said pumping chamber apart from said shoulder whereby depression of said pressure application zone causes fluid in said reservoir to flow against said mass causing said mass to separate from said shoulder and open a passage between said lower chamber and said pumping chamber and flow through said passage toward said outlet opening and into said channel.

24. The storage device of claim 23, wherein said limiting means comprise a plurality of protuberances formed in an inner wall of said tubular member.

25. The storage device of claim 24, wherein said tubular member includes notches formed in an annular lower surface to enable flow communication between said lower chamber and said reservoir.

26. The storage device of claim 23, wherein said covers each include a projection defining a conduit therein and arranged in the respective one of said cavities, said conduit being arranged to block said channel when said cover is closed and be in communication with said channel when said cover is open.

* * * * *